(12) United States Patent
Nguyen et al.

(10) Patent No.: US 9,156,916 B2
(45) Date of Patent: Oct. 13, 2015

(54) MODULATION OF T HELPER CELL-MEDIATED IMMUNE RESPONSES

(75) Inventors: Tue G. Nguyen, Ngunnawal (AU); Jonathan M. Morris, Longueville (AU); Eileen D. M. Gallery, Roseville (AU); Sharon McCracken, Ryde (AU)

(73) Assignees: The University of Sydney, Sydney (AU); Northern Sydney and Central Coast Area Health Service, Gosford (AU)

( * ) Notice: Subject to any disclaimer, the term of this patent is extended or adjusted under 35 U.S.C. 154(b) by 1158 days.

(21) Appl. No.: 12/298,275

(22) PCT Filed: Apr. 27, 2007

(86) PCT No.: PCT/AU2007/000379
§ 371 (c)(1),
(2), (4) Date: Jun. 12, 2009

(87) PCT Pub. No.: WO2007/124529
PCT Pub. Date: Nov. 8, 2007

(65) Prior Publication Data
US 2010/0028362 A1 Feb. 4, 2010

(30) Foreign Application Priority Data
Apr. 27, 2006 (AU) .................................. 2006902180

(51) Int. Cl.
*A61K 39/00* (2006.01)
*A61K 39/395* (2006.01)
*C07K 16/42* (2006.01)
*G01N 33/68* (2006.01)

(52) U.S. Cl.
CPC ........ *C07K 16/4283* (2013.01); *G01N 33/6854* (2013.01); *G01N 33/6863* (2013.01); *A61K 2039/505* (2013.01); *C07K 2317/76* (2013.01); *G01N 2800/24* (2013.01); *G01N 2800/52* (2013.01)

(58) Field of Classification Search
None
See application file for complete search history.

(56) References Cited

U.S. PATENT DOCUMENTS 5,298,420 A * 3/1994 Chang .......................... 435/328

FOREIGN PATENT DOCUMENTS

| WO | WO-92/06120 A1 | 4/1992 |
| WO | WO-92/07574 A1 | 5/1992 |
| WO | WO-03/004651 A1 | 1/2003 |

OTHER PUBLICATIONS

Morris et al., 2000, J. Immunol. vol. 164: 1734-1740.*
Form PCT/ISA/210 issued in PCT/AU2007/000379, Aug. 16, 2007, ISR.
Form PCT/IPEA/409 issued in PCT/AU2007/000379, Aug. 16, 2007, Report on Patentability.
Day, M.J. et al. Targeting autoantigen to B cells prevents the induction of a cell-mediated autoimmune disease in rats. *The Journal of Experimental Medicine*. 1992 vol. 175, No. 3, pp. 655-659.
Goroff, D.K. et al. Polyclonal activation of the murine immune system by an antibody to IgD. XI. Contribution of membrane IgD cross-linking to the generation of an in vivo polyclonal antibody response. *J Immunol*. 1991 vol. 146, No. 1, pp. 18-25.
Shirai, A. et al., Treatment with dextran-conjugated anti-IgD delays the development of autoimmunity in MRL-Ipr/Ipr mice. *J Immunol*. 1994 vol. 153, No. 4, pp. 1889-1894.
Wood, G.W. et al., A reevaluation of B-lymphocyte levels in peripheral blood from cancer patients. *Journal of the National Cancer Institute*, 1978 vol. 61, No. 3, pp. 715-718.
Weider, F. , Immunofluorescent investigations in cutaneous vasculitis. II. Histotopical demonstration of IgD and fibrin. *Archives for Dermatological Research*. 1975 vol. 254, No. 2, pp. 215-224.

* cited by examiner

*Primary Examiner* — Amy Juedes
(74) *Attorney, Agent, or Firm* — Locke Lord LLP; Jeffrey D. Hsi; Gabriel J. McCool

(57) ABSTRACT

Provided herein are methods for modulating one or more of a T-helper cell or monocyte lineage cell-mediated immune response in a subject, the method comprises administering to the subject an effective amount of a compound which binds to surface membrane immunoglobulin D (smIgD). Also provided are methods of diagnosis of one or more of a T-helper cell or monocyte lineage cell-mediated immune disease, and compositions and kits for use in such methods.

5 Claims, 9 Drawing Sheets

A

B

A - Unstimulated Monocytes

B - LPS alone, 4hrs

C - Anti-human smIgD Ab only, 24 hrs

D - Anti-human smIgD Ab + LPS, 4hrs

E - Anti-human smIgD Ab, 24hrs before LPS, 4hrs

SEQUENCE LISTING

```
<160> NUMBER OF SEQ ID NOS: 12

<210> SEQ ID NO 1
<211> LENGTH: 21
<212> TYPE: DNA
<213> ORGANISM: Homo sapiens

<400> SEQUENCE: 1
gggcgtccaa caatgtgacc c                                              21

<210> SEQ ID NO 2
<211> LENGTH: 21
<212> TYPE: DNA
<213> ORGANISM: Homo sapiens

<400> SEQUENCE: 2
cctggggaac cacatccttc g                                              21

<210> SEQ ID NO 3
<211> LENGTH: 24
<212> TYPE: DNA
<213> ORGANISM: Homo sapiens

<400> SEQUENCE: 3
```

```
gagcatgtga atgccatcca ggag                                            24
```

<210> SEQ ID NO 4
<211> LENGTH: 26
<212> TYPE: DNA
<213> ORGANISM: Homo sapiens

<400> SEQUENCE: 4

```
tcctggactg gctcccagca gtcaaa                                          26
```

<210> SEQ ID NO 5
<211> LENGTH: 24
<212> TYPE: DNA
<213> ORGANISM: Homo sapiens

<400> SEQUENCE: 5

```
cgggacgtgg agctggccga ggag                                            24
```

<210> SEQ ID NO 6
<211> LENGTH: 24
<212> TYPE: DNA
<213> ORGANISM: Homo sapiens

<400> SEQUENCE: 6

```
caccagctgg ttatctctca gctc                                            24
```

<210> SEQ ID NO 7
<211> LENGTH: 28
<212> TYPE: DNA
<213> ORGANISM: Homo sapiens

<400> SEQUENCE: 7

```
tgaaatatac aagttatatc ttggcttt                                        28
```

<210> SEQ ID NO 8
<211> LENGTH: 26
<212> TYPE: DNA
<213> ORGANISM: Homo sapiens

<400> SEQUENCE: 8

```
gatgctcttc gacctcgaaa cagcat                                          26
```

<210> SEQ ID NO 9
<211> LENGTH: 28
<212> TYPE: DNA
<213> ORGANISM: Homo sapiens

<400> SEQUENCE: 9

```
gaatggaatt aataattaca agaatccc                                        28
```

<210> SEQ ID NO 10
<211> LENGTH: 24
<212> TYPE: DNA
<213> ORGANISM: Homo sapiens

<400> SEQUENCE: 10

```
tgtttcagat ccctttagtt ccag                                            24
```

<210> SEQ ID NO 11
<211> LENGTH: 19
<212> TYPE: DNA
<213> ORGANISM: Homo sapiens

<400> SEQUENCE: 11

```
accccactga aaaagatga                                                19

<210> SEQ ID NO 12
<211> LENGTH: 20
<212> TYPE: DNA
<213> ORGANISM: Homo sapiens

<400> SEQUENCE: 12
atcttcaaac ctccatgatg                                               20
```

MODULATION OF T HELPER CELL-MEDIATED IMMUNE RESPONSES

This application is the U.S. national phase, pursuant to 35 U.S.C. §371, of PCT international application Ser. No. PCT/AU2007/000379, filed Apr. 27, 2007, designating the United States and published in English on Nov. 8, 2007 as publication WO 2007/124529 A1, which claims priority to Australian application Ser. No. 2006902180, filed Apr. 27, 2006. The entire contents of the aforementioned patent applications are incorporated herein by this reference.

TECHNICAL FIELD

The present invention relates to methods, compositions and kits for the treatment and/or diagnosis of diseases caused by aberrant T-helper cell (Th) or monocyte cell-mediated immune responses. In addition, the present invention relates to methods, compositions and kits for determining the susceptibility of a subject to a disease, monitoring the responsiveness of a subject to therapy, and screening candidate molecules for capacity to modulate a T-helper cell or monocyte-mediated immune response.

RELATED APPLICATION

The present application claims benefit to Australian provisional patent application No. 2006902180, filed 27 Apr. 2006, the entire contents of which is incorporated herein by reference.

BACKGROUND

The differentiation of naïve $CD4^+$ T-cells into $T_{helper}$ (Th) cells is a central process that plays a crucial and determinant role in directing the type of immune responses that develop against pathogenic and non-self antigens in humans. There are two principal types of immune response, namely type-1 (Th1) and type-2 (Th2), which are categorized on the basis of the cytokine profiles that these responses produce and by the class of Th cells which contribute to the immune response.

Th1 cells secrete mainly interleukin-2 (IL-2), interferon-gamma (IFN-$\gamma$), granular macrophage-colony stimulating factor (GM-CSF), and tumour necrosis factor-alpha (TNF-$\alpha$). These cytokines are the essential factors for the initiation of cell-mediated immunities that involve the activation of cytotoxic $CD8^+$ T-cells, natural killer (NK) cells, monocytes and macrophages. Th1 immunity also involves the direct activation of naïve $CD8^+$ $T_{cytotoxic}$-cells (Tc) by signalling through T-cell receptors (TCR), which in turn recognize non-self or pathogenic antigens presented by major histocompatibility complex class I (MHC-I) on antigen-presenting cells (APC). Once they are activated, naïve $CD8^+$ Tc-cells differentiate into long-term Tc-effector and Tc-memory cells, which carry out the cytotoxic killing of pathogens.

Th2 cells produce mainly IL-4, IL-5, IL-10 and IL-13 that are primarily involved in the initiation of humoral immune responses.

The differentiation of naïve $CD4^+$ Th-cells is initiated when their TCR encounters and locks on to an antigen bound to the MHC-class II (MHC-II) on an APC. In conjunction with the activation of co-stimulatory pathways, stimulation of the TCR delivers a signal which is mediated through the activation of the protein kinase C (PKC) pathway, that in turn promotes the differentiation of naïve $CD4^+$ T-cells into Th-progenitor cells. At this stage of differentiation, progenitor Th-cells have the capability to differentiate into either Th1 or Th2 cells, depending on the cytokine environment. Upon exposure to IL-12, IL-18, IL-23, IL-27 or IFN-$\gamma$, Th-progenitor cells are driven toward the Th1 lineage commitment, whereas in the presence of IL-4 or IL-10, the Th-progenitor cells are programmed to develop into Th2 lineage.

It is also significant to note that Th1 and Th2 cytokines have a cross-inhibitory action on each other. This regulatory interaction between Th1 and Th2 signals appears to act as a mechanism to shift the balance toward a particular lineage commitment.

Appropriate induction of Th1 immunity is essential for fighting infection by invading bacterial and viral pathogens. The production of Th1 cytokines plays a crucial role in the function of Th1 immunity as a mechanism to fight pathogens and also to participate in tumour surveillance.

Several transcription factors have been identified as important regulators of Th1 lineage development. These include STAT-1, STAT-4, NF-kB, IRF-1, T-bet (or Tbx21) and members of the Ets family.

However, excessive production of Th1 cytokines has been associated with autoimmune diseases. Th1 immunity is also a key mediator of the 'cytokine storm' that often causes fatality in severe cases of infectious diseases such as pneumonia and 'bird flu'. The mechanisms of the pathogenesis of autoimmune diseases and inflammatory conditions involves the production of Th1 cytokines, activation and recruitment of $CD4^+$ Th cells, $CD8^+$ Tc cells, natural killer (NK) cells and other components of the immune system such as macrophages. Accordingly, elevated expression of T-bet and Th1-cytokines are central to mediating the pathological processes of many autoimmune diseases, acute and chronic inflammatory conditions, solid organ transplant rejection, graft-versus-host disease in bone marrow transplantation, rejection of embryo implantation after IVF and a range of other diseases and pathologies.

There are a number of immuno-suppressive/anti-inflammatory agents and different therapies currently used for Th1-related diseases and organ transplantation in the clinic as well as showing promising therapeutic potential in pre-clinical stage. These include steroid hormones and their analogues (estrogen, progesterone, human growth hormones, glucocorticoids, dexamethasone), small chemical molecules, non-steroidal anti-inflammatory drugs (NSAIDs), cyclosporine, rapamycin, sulfasalazine, methotrexate, calcineurin inhibitors, COX-2 inhibitors, antibodies against specific cytokines and their receptors (anti-TNF$\alpha$ antibody [Infliximab], anti-costimulatory molecule antibody, anti IL-2 receptor antibody [Daclizumab], anti-IL12 antibody). However, there are a number of problems with the use of these immuno-suppressive drugs.

Firstly, these drugs have significant side-effects that particularly associated with chronic use. For example, nephrotoxicity is associated with calcineurin inhibitors, hypertension and cardiovascular diseases with the use of corticosteroids. There is a significantly increased risk of breast cancer and ovarian cancer from the use of steroid hormones, an increased risk of development of haematologic neoplasms and kidney problems with chronic use of infliximab, and cytotoxicity with the use of methotrexate and rapamycin.

Secondly, there are major concerns and problems over long-term graft survival and chronic graft rejection with prolonged exposure to these drugs. This is evidenced by the fact that although the use of immuno-suppressive drugs improves 1-year graft survival from 45% to about 80-90% for most organ transplants, long-term graft survival (5 years or more) has changed little, remaining at around 50-60%. Another example is the use of cyclosporine in the prevention of graft-versus-host disease in bone marrow transplantation. Its use is highly effective in the clinical setting. However, patients often relapse due to the inhibitory action of cyclosporine on the graft-versus-leukaemia action by the donor marrow. There are also cytotoxic effects and a risk of renal damage associated with chronic use of cyclosporine. This compromises the clinical benefit of bone marrow transplantation in leukaemia patients. Also, these immuno-suppressive drugs have to be administered regularly and over a prolonged period of time.

Intra-venous injection of pooled serum immunoglobulins, also known as intra-gam, from thousands of volunteers has also been used to treat a wide range of immune-related disorders. However, this treatment requires a large pool of serum, in the order of tens of thousand of donors, with the isolation of serum immunoglobulins being an inefficient and costly process. Since immunoglobulins used in such treatments are isolated from human serum, there are also risks of transmission of diseases from donors to patients. Thus, the clinical benefits and the cost effectiveness of such treatments remain limited.

Hence, there remains a requirement for new approaches to the treatment of autoimmune diseases, inflammatory diseases and allergy-related diseases.

SUMMARY OF THE INVENTION

The present invention is based on the unexpected and surprising finding that the specific binding of surface membrane IgD (smIgD), for example using an anti-IgD antibody, can inhibit the PMA/Ionomycin-induced expression of the Th1 cytokines GM-CSF and TNF-α and the transcription factor T-Bet, the master regulator of Th1 development, by cells present in the peripheral blood mononuclear cell fraction and by a Jurkat T cell line. The binding of surface membrane smIgD was also found to inhibit lipopolysachharide-induced TNF-α expression by CD14+ cells from the peripheral blood mononuclear cell fraction, which are considered to be cells of the monocyte lineage.

The suppressive effects of binding to human smIgD on Th1 immune components which are involved in the pathway leading to an immune response, and which have strong links with the pathogenesis of a wide range of autoimmune diseases, presents new methods for the treatment and/or diagnosis of diseases caused by aberrant T-helper cell (Th)-mediated and/or monocyte cell lineage-mediated immune responses, including inflammatory responses, and for determining the susceptibility of a subject to a disease, monitoring the responsiveness of a subject to therapy, and screening candidate molecules for capacity to modulate a T-helper cell-mediated and/or monocyte cell lineage mediated immune response.

According to a first aspect of the present invention, there is provided a method for modulating an immune response in a subject which is mediated by any one or more of a T-helper cell or monocyte lineage cell, wherein the method comprises administering to the subject an effective amount of a compound which binds to surface membrane immunoglobulin D (smIgD).

The T-helper cell or monocyte lineage cell-mediated immune response may comprise an autoimmune disease, an inflammatory response or an allergic disease.

The compound may comprise an anti-smIgD antibody, an anti-IgD antibody, an anti-Ig delta chain antibody, an antigen, a protein, an inorganic compound or any combination thereof.

The antigen may be a self-antigen. The self-antigen may be expressed on the surface of a cell. The cell may be endogenous to the subject.

In one embodiment the surface membrane IgD is present on a T-helper cell. In another embodiment, the surface membrane IgD is present on a cell of monocyte lineage, such as a monocyte or a macrophage. The binding of the compound to smIgD may result in cross-linking of the smIgD to other smIgD on the cell, or to other molecules on the cell. Additionally or alternatively, the binding of the compound to smIgD may result in the activation of the cell which carries the smIgD. The binding of the compound to smIgD may result in suppression of expression of at least one molecule selected from the group comprising GM-CSF, TNF-α and T-Bet. The suppression of expression of the at least one molecule may result in suppression of a Th1 immune response. Additionally, the suppression of expression of the at least one molecule may result in activation of a Th2 immune response.

The method may further comprise administration of a further molecule, wherein the further molecule contributes to modulating the T-helper cell or monocyte lineage cell-mediated immune response.

According to a second aspect of the present invention, there is provided a method for diagnosing one or more of a T helper cell or monocyte lineage cell-mediated immune disease in a subject, wherein the method comprises:
(a) obtaining a biological sample from the subject; and
(b) quantifying the level of expression of surface membrane immunoglobulin D (smIgD) in the sample
wherein the level of expression of smIgD is indicative of the presence or absence of a T helper cell-mediated immune disease.

According to a third aspect of the present invention, there is provided a method for diagnosing one or more of a T helper cell or monocyte lineage cell-mediated immune disease in a subject, wherein the method comprises:
(a) obtaining a biological sample from the subject;
(b) contacting the biological sample with a compound that binds to surface membrane immunoglobulin D (smIgD); and
(c) assaying for the level of expression of at least one molecule selected from the group comprising GM-CSF, TNF-α and T-Bet
wherein the level of expression of the at least one molecule selected from the group comprising GM-CSF, TNF-α and T-Bet is indicative of the presence or absence of a T helper cell or monocyte lineage cell-mediated immune disease.

According to a fourth aspect of the present invention, there is provided a method for determining the susceptibility of a subject to one or more of a T helper cell or monocyte lineage cell-mediated immune disease, wherein the method comprises:
(a) obtaining a biological sample from the subject; and
(b) quantifying the level of expression of surface membrane immunoglobulin D (smIgD) in the sample
wherein the level of expression of smIgD is indicative of the susceptibility of the subject to a T helper cell or monocyte lineage cell-mediated immune disease.

According to a fifth aspect of the present invention, there is provided a method for determining the susceptibility of a subject to one or more of a T helper cell or monocyte lineage cell-mediated immune disease, wherein the method comprises:
(a) obtaining a biological sample from the subject;
(b) contacting the biological sample with a compound that binds to surface membrane immunoglobulin D (smIgD); and (c) assaying for the level of expression of at least one molecule selected from the group comprising GM-CSF, TNF-α and T-Bet
wherein the level of expression of the at least one molecule selected from the group comprising GM-CSF, TNF-α and T-Bet is indicative of the susceptibility of the subject to a T helper cell or monocyte lineage cell-mediated immune disease.

According to a sixth aspect of the present invention, there is provided a method for monitoring the responsiveness of a subject to therapy for a T helper cell or monocyte lineage cell-mediated immune disease, wherein the method comprises:
(a) obtaining a biological sample from the subject; and
(b) quantifying the level of expression of surface membrane immunoglobulin D (smIgD) in the sample
wherein the level of expression of smIgD is indicative of the responsiveness of the subject to therapy for a T helper cell or monocyte lineage cell-mediated immune disease.

According to a seventh aspect of the present invention, there is provided a method for monitoring the responsiveness of a subject to therapy for one or more of a T helper cell or monocyte lineage cell-mediated immune disease, wherein the method comprises:
(a) obtaining a biological sample from the subject;
(b) contacting the biological sample with a compound that binds to surface membrane immunoglobulin D (smIgD); and
(c) assaying for the level of expression of at least one molecule selected from the group comprising GM-CSF, TNF-α and T-Bet
wherein the level of expression of the at least one molecule selected from the group comprising GM-CSF, TNF-α and T-Bet is indicative of the responsiveness of the subject to therapy for a T helper cell or monocyte lineage cell-mediated immune disease.

According to an eighth aspect of the present invention, there is provided a method for screening at least one candidate molecule for its capacity to modulate one or more of a T-helper cell or monocyte lineage cell-mediated immune response, wherein the method comprises:
(a) contacting the at least one candidate molecule with a biological sample; and
(b) assaying for the level of binding of the at least one candidate molecule to surface membrane immunoglobulin D (smIgD) in the sample
wherein the level of binding of the at least one candidate molecule to smIgD is indicative of the capacity of the at least one candidate molecule to modulate a T-helper cell or monocyte lineage cell-mediated immune response.

According to a ninth aspect of the present invention, there is provided a method for screening at least one candidate molecule for its capacity to modulate one or more of a T-helper cell or monocyte lineage cell-mediated immune response, wherein the method comprises:
(a) contacting the at least one candidate molecule with a biological sample; and
(b) assaying for the level of expression of at least one molecule selected from the group comprising GM-CSF, TNF-α and T-Bet
wherein the level of expression of the at least one molecule selected from the group comprising GM-CSF, TNF-α and T-Bet is indicative of the capacity of the at least one candidate molecule to modulate a T-helper cell or monocyte lineage cell-mediated immune response.

According to a tenth aspect of the present invention, there is provided a compound that binds to surface membrane immunoglobulin D (smIgD) when used for modulating one or more of a T-helper cell or monocyte lineage cell-mediated immune response in a subject, together with a pharmaceutically acceptable carrier, diluent or excipient.

According to an eleventh aspect of the present invention, there is provided a compound that binds to surface membrane immunoglobulin D (smIgD) when used for:
(a) diagnosing a T helper cell or monocyte lineage cell-mediated immune disease in a subject;
(b) determining the susceptibility of a subject to a T helper cell or monocyte lineage cell-mediated immune disease; or
(c) monitoring the responsiveness of a subject to therapy for a T helper cell or monocyte lineage cell-mediated immune disease;
wherein the steps of (a), (b) or (c) are achieved by assaying for the level of expression of at least one molecule selected from the group comprising GM-CSF, TNF-α and T-Bet in a biological sample from the subject
together with a pharmaceutically acceptable carrier, diluent, excipient and/or adjuvant.

According to a twelfth aspect of the present invention, there is provided use of a compound that binds to surface membrane immunoglobulin D (smIgD) in the methods of the first to seventh aspects.

According to a thirteenth aspect of the present invention, there is provided use of a molecule screened by the methods of the eighth or ninth aspects in the methods of the first to seventh aspects.

According to a fourteenth aspect of the present invention, there is provided a kit for modulating a T-helper cell or monocyte lineage cell-mediated immune response in a subject, wherein the kit comprises a compound that binds to surface membrane immunoglobulin D (smIgD).

According to a fifteenth aspect of the present invention, there is provided a kit for:
(a) diagnosing a T helper cell or monocyte lineage cell-mediated immune disease in a subject;
(b) determining the susceptibility of a subject to a T helper cell or monocyte lineage cell-mediated immune disease; or
(c) monitoring the responsiveness of a subject to therapy for a T helper cell or monocyte lineage cell-mediated immune disease;
wherein the kit comprises:
(a) means for obtaining a biological sample from the subject; and
(b) means for quantifying the level of expression of surface membrane immunoglobulin D (smIgD)
wherein level of expression of surface membrane immunoglobulin D (smIgD) is indicative of a T helper cell or monocyte lineage cell-mediated immune disease in a subject, the susceptibility of a subject to a T helper cell or monocyte lineage cell-mediated immune disease or the responsiveness of a subject to therapy for a T helper cell or monocyte lineage cell-mediated immune disease.

According to a sixteenth aspect of the present invention, there is provided a kit for screening at least one candidate molecule for its capacity to modulate a T-helper cell or monocyte lineage cell-mediated immune response, wherein the kit comprises:
(a) means for contacting the at least one candidate molecule with a biological sample; and
(b) means for assaying for the level of binding of the at least one candidate molecule to surface membrane immunoglobulin D (smIgD) in the sample
wherein the level of binding of the at least one candidate molecule to smIgD is indicative of the capacity of the at least one candidate molecule to modulate a T-helper cell or monocyte lineage cell-mediated immune response.

According to a seventeenth aspect of the present invention, there is provided a kit for screening at least one candidate molecule for its capacity to modulate a T-helper cell or monocyte lineage cell-mediated immune response, wherein the kit comprises:
(a) means for contacting the at least one candidate molecule with a biological sample; and
(b) means for assaying for the level of expression of at least one molecule selected from the group comprising GM-CSF, TNF-α and T-Bet
wherein the level of expression of the at least one molecule selected from the group comprising GM-CSF, TNF-α and T-Bet is indicative of the capacity of the at least one candidate molecule to modulate a T-helper cell or monocyte lineage cell-mediated immune response.

Abbreviations

Ab antibody
APC antigen presenting cells
GM-CSF granulocyte macrophage colony stimulating factor
IFN interferon
IL interleukin
IVF in vitro fertilization
NK cells natural killer cells
PBMC peripheral blood mononuclear cells
PBS-E endotoxin-free phosphate buffer saline
PKC protein kinase C
PMA phorbol myristate acetate
RT-PCR reverse transcriptase polymerase chain reaction
smIgD surface membrane immunoglobulin D
T-Bet T-box expressed in T cells, also known as Tbx21
$T_c$ cells $T_{cytotoxic}$ cells
TGF-β transforming growth factor-β
Th cells $T_{helper}$ cells
TNF-α tumour necrosis factor-α

Definitions

In the context of this specification, the term "comprising" means "including principally, but not necessarily solely". Furthermore, variations of the word "comprising", such as "comprise" and "comprises", have correspondingly varied meanings.

As used herein the terms "treating" and "treatment" refer to any and all uses which remedy a condition or symptoms, prevent the establishment of a condition or disease, or otherwise prevent, hinder, retard, ameliorate or reverse the progression of a condition or disease or other undesirable symptoms in any way whatsoever.

As used herein the term "effective amount" includes within its meaning a sufficient amount of an agent or compound to provide the desired effect. In a particular embodiment, the effective amount is an amount sufficient to provide the desired effect while being substantially non-toxic. The exact amount required will vary from subject to subject depending on factors such as the species being treated, the age and general condition of the subject, the particular agent being administered and the mode of administration and so forth. Thus, it is not possible to specify an exact "effective amount". However, for any given case, an appropriate "effective amount" may be determined by one of ordinary skill in the art using only routine experimentation.

As used herein, the term "antibody" includes antibody fragments, including but not limited to, heavy chains, light chains, variable regions, constant regions, Fab, Fc, Fc receptors, single chain (scFV) antibodies, complementarity determining regions (CDRs) and any protein, polypeptide or peptide comprising an antibody, or part thereof.

As used herein, the term "modulation", when used in relation to an immune response, may refer to the activation, initiation, or increase of an immune response, or the inhibition, suppression, blocking or decrease of an immune response.

As used herein the term "soluble" as it pertains to the IgD means any form of IgD that retains the ability to bind a ligand but is not membrane-bound. "Surface membrane IgD" or "smIgD" refers to a form of IgD which is bound on the plasma membrane of a cell. It may be a membrane-bound form of IgD or a secreted form of IgD which is bound to a plasma membrane. The smIgD may be expressed by the cell. In other embodiments, the smIgD is exogenous to the cell but is bound to the cell plasma membrane, for example via an Fc receptor expressed by the cell on the plasma membrane.

BRIEF DESCRIPTION OF THE FIGURES

Embodiments of the present invention will now be described, by way of example only, with reference to the accompanying figures.

BEST MODE OF PERFORMING THE INVENTION

Figure 1:
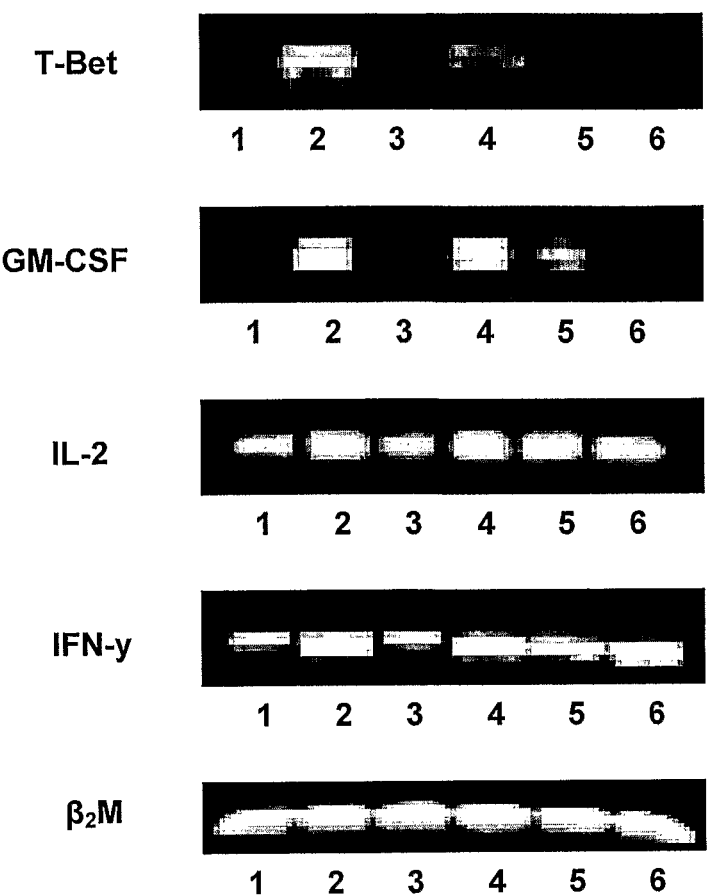
FIG. 1 provides images of the results of a representative RT-PCR analysis of Th1-related cytokine mRNA expression in the Jurkat T-cell line following treatment with anti-human smIgD Ab and PMA/Ionomycin. Cells were pre-treated with anti-human smIgD Ab at various time points prior to stimulation with PMA and Ionomycin for 4 hrs. Lane 1: solvent control; Lane 2: 20 ng/ml PMA and 500 ng/ml Ionomycin, 4 hrs; Lane 3: 50 µg/ml anti-human smIgD Ab, 24 hrs; Lane 4: 50 µg/m anti-human smIgD Ab and PMA/Ionomycin, 4 hrs: Lane 5: 50 µg/m Anti-human smIgD Ab, 24 hrs and then PMA/Ionomycin, 4 hrs; Lane 6: 50 µg/m anti-human smIgD Ab and 50 ng/ml TGF-β1, 24 hrs and then PMA/Ionomycin, 4 hrs. $β_2M$ gene expression was used as an internal quality and loading control. This figure is a representative of 2 or more independent experiments.

The inventors have demonstrated an unexpected and surprising suppression of cell activation via the protein kinase C pathway following the binding of human surface-membrane IgD (smIgD). In particular, the inventors have showed that the binding of smIgD by an anti-smIgD antibody in human PBMC inhibits the PMA/Ionomycin-induced expression of the Th1 cytokines GM-CSF, TNF-α and the transcription factor T-Bet, the master regulator of Th1 development. Also demonstrated is the suppression of LPS stimulated expression of the pro-inflammatory cytokine TNF-α by CD14-labelled cells, presumably cells of monocyte lineage, from a PBMC population by exposure to an anti-smIgD antibody. The binding of human smIgD by an antibody can suppress the expression of a central regulatory factor and of components of the human Th1 immune response which are normally upregulated upon activation of human immune cells. The suppressive effects of the binding of an antibody to human smIgD on these Th1 immune components, which have strong links with the pathogenesis of a wide range of autoimmune diseases, offers new methods for the treatment and/or diagnosis of diseases caused by aberrant induction of T-helper cell (Th)-mediated immune responses, and for determining the susceptibility of a subject to a disease, monitoring the responsiveness of a subject to therapy, and screening candidate molecules for capacity to modulate a T-helper cell-mediated immune response.

The activation of immune cells, including B cells, macrophages and dendritic cells, is mediated by protein kinase C (PKC) pathways. Such pathways play an essential role in mediating and regulating many aspects of human immune responses. As described herein, the potent pan-activators of PKC isoforms, PMA and Ionomycin, were used as artificial stimuli for activation of immune cells and for inducing cytokine gene expression. 9PMA and Ionomycin are pro-inflammatory agents and potent inducers of Th1 immunity in animal models.

As demonstrated in this study, the expression of a central regulator of Th1 immunity, and of some of the classical Th1 cytokines, whose expressions have been well-demonstrated to be associated with clinical severity and pathogenic progression of a wide range of autoimmune diseases, has been suppressed through administration of an antibody specific for smIgD. Through binding to smIgD, this antibody cross-links or activates a signal that suppresses the induction of T-Bet, TNF-α and GM-CSF expression upon immunological activation. Hence, the inventors have demonstrated specific suppression of the amplification of Th1 signals mediated by the induction of T-bet expression during immune cell activation. They have also demonstrated specific suppression of the classical Th1 cytokines, TNF-α and GM-CSF, thereby blocking the involvement of these cytokines in the pathogenesis of inflammatory and immunological conditions.

In one embodiment, the methods, compositions and/or kits may involve suppression of the amplification signal mediated by the induction of T-bet expression during the activation of immune cells via the protein kinase C pathway.

In another embodiment, the methods, compositions and/or kits may involve suppressing two key Th1 cytokines, TNFα and GM-CSF, involved in the pathogenesis of over-activation of Th1 immunity.

Accordingly, the methods, compositions and/or kits disclosed herein may involve the use of anti-smIgD antibodies to suppress T-Bet, TNF-α, GM-CSF, leading to the suppression of over-activation of Th1 immune responses. Suppression of the amplification signal mediated by T-bet may reduce Th1 responses as well as promote Th2 responses. Suppression of TNF-α and GM-CSF may suppress effector functions of Th1 immune responses. Further, the methods, compositions and/or kits disclosed herein may involve the use of anti-smIgD antibodies to suppress inflammation responses, including inflammation associated with the activation of monocytes.

The methods, compositions and/or kits disclosed herein therefore have particular application for both the suppression of Th1 immune responses and the promotion of Th2 immune responses, including antibody production.

Methods

The present invention provides methods for modulating a immune response and/or an inflammatory response in a subject which is mediated by T-helper cells or cells of monocyte lineage, wherein the methods comprise administering to the subject an effective amount of a compound which binds to surface membrane immunoglobulin D (smIgD).

A T helper cell-mediated immune or inflammatory disease may comprise an autoimmune disease, an inflammatory disease or an allergic disease. The autoimmune disease, inflammatory disease or allergic disease may be selected from the group comprising atherosclerosis, type-1 diabetes mellitus, multiple sclerosis, encephalomyelitis, thyroiditis, arthritis (rheumatoid arthritis, osteoarthritis, psoriatic arthritis), dermatitis (atopic dermatitis, eczematous dermatitis), asthma, acne, psoriasis, uveitis, Crohn's disease, ulcerative colitis, ulcers, conjunctivitis, chronic pancreatitis, chronic hepatitis, Kawasaki disease, cerebral malaria, systematic lupus erythematosis, conjunctivitis, nephritis, asthma, interstitial lung fibrosis, chronic bronchitis, destruction of lung tissues during infection of 'avian flu' and pneumonia, graft versus host diseases, solid organ transplant rejection, pre-eclampsia, spontaneous abortion and rejection of IVF implantation.

A monocyte lineage cell mediated-immune or inflammatory disease may involve monocyte release of TNF-α. It may be selected from the group consisting of rheumatoid arthritis, osteomyelitis, osteoarthritis, ulcerative colitis, inflammatory lesions, infections of the skin, Crohn's disease, pulmonary fibrosis, sarcoidosis, systemic sclerosis, organ transplant rejection lupus erythematosus, glomerulonephritis, inflammations of the skin, atherosclerosis, pre-eclampsia, hypertension in pregnancy, chronic inflammation and conditions caused by sepsis.

The compound may comprise an anti-smIgD antibody, an antigen, a protein, an inorganic compound or any combination thereof. The antigen may be a self-antigen. The self-antigen may be expressed on the surface of a cell. The cell may be endogenous to the subject. Accordingly, the compound may comprise a self-antigen expressed on the surface of a cell that is endogenous to the subject being treated. Such compound may be derived through standard techniques well known to those of skill in the art, including but not limited to, autologous cell transfer or adoptive transfer, for example, involving T cells, B cells, dendritic cells or other antigen-presenting cells endogenous to the subject being treated.

The binding of the compound to smIgD may result in cross-linking of smIgD. The binding of the compound to smIgD may result in suppression of expression of at least one molecule selected from the group comprising GM-CSF, TNF-α and T-Bet. The suppression of expression of the at least one molecule may result in suppression of a Th1 immune response. Additionally, the suppression of expression of the at least one molecule may result in activation of a Th2 immune response.

The methods may further comprise administration of a further molecule, wherein the further molecule contributes to modulating the T-helper cell or a monocyte lineage cell-mediated immune response. Such further molecule may comprise any compound that is known in the art as therapeutic for an autoimmune disease, an inflammatory disease or an allergic disease, for example, any of the diseases described above.

The present invention also provides methods for diagnosing a T helper cell or monocyte lineage cell-mediated immune disease in a subject, for determining the susceptibility of a subject to a T helper cell or monocyte lineage cell-mediated immune disease and for monitoring the responsiveness of a subject to therapy for a T helper cell or monocyte lineage cell-mediated immune disease, wherein the methods comprise obtaining a biological sample from the subject and quantifying the level of expression of surface membrane immunoglobulin D (smIgD) in the sample, wherein the level of expression of smIgD is indicative of the presence or absence of a T helper cell or monocyte lineage cell-mediated immune disease in a subject, indicative of the susceptibility of a subject to a T helper cell or a monocyte lineage cell-mediated immune disease or indicative of the responsiveness of a subject to therapy for a T helper cell or a monocyte lineage cell-mediated immune disease, respectively.

Other methods for diagnosing a immune and/or inflammatory disease in a subject are also contemplated, including for determining the susceptibility of a subject to a T helper cell and/or monocyte cell lineage-mediated immune and/or inflammatory disease and for monitoring the responsiveness of a subject to therapy, wherein the methods comprise obtaining a biological sample from the subject, contacting the biological sample with a compound that binds to surface membrane immunoglobulin D (smIgD) and assaying for the level of expression of at least one molecule selected from the group comprising GM-CSF, TNF-α and T-Bet, wherein the level of expression of the at least one molecule selected from the group comprising GM-CSF, TNF-α and T-Bet is indicative of the presence or absence of a T helper cell and/or monocyte cell lineage-mediated immune and/or inflammatory disease in a subject, or is indicative of the susceptibility of a subject to the disease or indicative of the responsiveness of a subject to therapy for the disease, respectively.

The present invention additionally provides method for screening at least one candidate molecule for its capacity to modulate a T-helper cell or a monocyte lineage cell-mediated immune response, wherein the methods comprise contacting the at least one candidate molecule with a biological sample and assaying for the level of binding of the at least one candidate molecule to surface membrane immunoglobulin D (smIgD) in the sample, wherein the level of binding of the at least one candidate molecule to smIgD is indicative of the capacity of the at least one candidate molecule to modulate a T-helper cell or a monocyte lineage cell-mediated immune response.

Other methods for screening at least one candidate molecule for its capacity to modulate a T-helper cell and/or monocyte-mediated immune and/or inflammatory response are also contemplated as within the scope of the present invention, wherein the methods comprise contacting the at least one candidate molecule with a biological sample and assaying for the level of expression of at least one molecule selected from the group comprising GM-CSF, TNF-α and T-Bet, wherein the level of expression of the at least one molecule selected from the group comprising GM-CSF, TNF-α and T-Bet is indicative of the capacity of the at least one candidate molecule to modulate a T-helper cell and/or monocyte cell lineage-mediated immune and/or inflammatory response.

Compounds and Uses Thereof

The present invention provides compounds that bind to surface membrane immunoglobulin D (smIgD) when used for modulating a T-helper cell-mediated immune response in a subject, together with a pharmaceutically acceptable carrier, diluent or excipient.

The present invention also provides compounds that bind to surface membrane immunoglobulin D (smIgD) when used for diagnosing a T helper cell or a monocyte lineage cell-mediated immune disease in a subject, determining the susceptibility of a subject to a T helper cell or a monocyte lineage cell-mediated immune disease or monitoring the responsiveness of a subject to therapy for a T helper cell or a monocyte lineage cell-mediated immune disease (wherein these uses are achieved by assaying for the level of expression of at least one molecule selected from the group comprising GM-CSF, TNF-α and T-Bet in a biological sample from the subject) together with a pharmaceutically acceptable carrier, diluent, excipient and/or adjuvant.

The present invention further provides use of compounds that bind to surface membrane immunoglobulin D (smIgD) in the methods as described herein.

The present invention moreover provides a use of a molecule screened by the methods as described herein in the methods for modulating a T-helper cell or a monocyte lineage cell-mediated immune response in a subject, for diagnosing a T helper cell or a monocyte lineage cell-mediated immune disease in a subject are also contemplated, for determining the susceptibility of a subject to a T helper cell or a monocyte lineage cell-mediated immune disease and for monitoring the responsiveness of a subject to therapy for a T helper cell or a monocyte lineage cell-mediated immune disease as described herein.

The compounds may comprise an anti-smIgD antibody, an antigen, a protein, an inorganic compound or any combination thereof as detailed elsewhere herein.

Antibodies to Surface Membrane Immunoglobulin D (smIgD)

Particular embodiments of the invention provide for the use of one or more antibodies raised against surface membrane immunoglobulin D (smIgD). The antibodies may be polyclonal or monoclonal and may be raised by the use of smIgD or an antigenic fragment or portion thereof as an antigen. Suitable antibodies include, but are not limited to polyclonal, monoclonal, chimeric, humanised, single chain, Fab fragments, and Fab expression libraries.

Suitable antibodies may be prepared from discrete regions or fragments of surface membrane immunoglobulin D (smIgD). Methods for the generation of suitable antibodies will be readily appreciated by those skilled in the art. For example, an anti-smIgD monoclonal antibody, typically containing Fab portions, may be prepared using the hybridoma technology described in Antibodies—A Laboratory Manual, Harlow and Lane, eds., Cold Spring Harbour Laboratory, N.Y. (1988). In essence, in the preparation of monoclonal antibodies directed toward smIgD, a fragment or analogue thereof, any technique that provides for the production of antibody molecules by continuous cell lines in culture may be used. These include the hybridoma technique originally developed by Kohler et al., Nature, 256:495-497 (1975), as well as the trioma technique, the human B-cell hybridoma technique [Kozbor et al., Immunology Today, 4:72 (1983)], and the EBV-hybridoma technique to produce human monoclonal antibodies [Cole et al., in Monoclonal Antibodies and Cancer Therapy, pp. 77-96, Alan R. Liss, Inc., (1985)]. Immortal, antibody-producing cell lines can be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies and T-cell Hybridomas" (1981); Kennett et al., "Monoclonal Antibodies" (1980).

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Similarly, there are various procedures known in the art which may be used for the production of polyclonal antibodies to smIgD, or fragments or analogues thereof. For the production of polyclonal antibodies, various host animals can be immunized by injection with the IgD polypeptide, or a fragment or analogue thereof, including but not limited to rabbits, mice, rats, sheep, goats, etc. Further, an IgD polypeptide or fragment or analogue thereof can be conjugated to an immunogenic carrier, e.g., bovine serum albumin (BSA) or keyhole limpet hemocyanin (KLH). Also, various adjuvants may be used to increase the immunological response, including but not limited to Freund's (complete and incomplete), nitrocellulose, cellulose acetate, mineral gels such as aluminium hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

Screening for the desired antibody can also be accomplished by a variety of techniques known in the art. Assays for immunospecific binding of antibodies may include, but are not limited to, radioimmunoassays, ELISAs (enzyme-linked immunosorbent assay), sandwich immunoassays, immunoradiometric assays, gel diffusion precipitation reactions, immunodiffusion assays, in situ immunoassays, Western and dot blots, precipitation reactions, agglutination assays, complement fixation assays, immunofluorescence assays, protein A assays, and immunoelectrophoresis assays, biosensors and the like (see, for example, Ausubel et al., eds, 1994, Current Protocols in Molecular Biology, Vol. 1, John Wiley & Sons, Inc., New York).

Detection of Antibody Binding

Antibody binding may be detected by virtue of a detectable label on a primary anti-surface membrane immunoglobulin D (smIgD) antibody. Alternatively, an anti-smIgD antibody may be detected by virtue of its binding with a secondary antibody or reagent that is appropriately labelled to enable detection. A variety of methods are known in the art for detecting binding in an immunoassay and are within the scope of the present invention. For example determinations of smIgD levels can be accomplished by any one of a number of techniques known in the art including, for example enzyme-linked immunosorbent assays (ELISA); sandwich immunoassays, competitive immunoassays, immunoradiometric assays (IRMA), radioimmunoassays (RIA), immunoelectrophoresis assays, in situ immunoassays, immunodiffusion assays, immunofluorescence assays, Western blots, ligand-binding assays, biosensors and the like.

Detection of GM-CSF, TNF-α and T-Bet Expression

Methods for determining the level of expression of genes of interest, for example GM-CSF, TNF-α and T-Bet, are exemplified herein and may include but are not limited to phosphor-imaging, RT-PCR, semi-quantitative PCR or real time RT-PCR. These methods are known to those of skill in the art.

Determination of smIgD, GM-CSF, TNF-α and T-Bet Levels

Methods of the invention for determining the significance of smIgD, GM-CSF, TNF-α and T-Bet levels may include the step of comparing the level of smIgD in a sample obtained from the subject of interest, for example an individual suspected of having an autoimmune disease, an inflammatory disease or an allergic disease, or a predisposition thereto, with the level of smIgD from one or more control samples. Typically the control sample may be a sample from an individual with normal levels of smIgD and/or known not to have an autoimmune disease, an inflammatory disease or an allergic disease.

Kits

The present invention also provides kits for the determination of the level of smIgD, wherein the kits facilitate the employment of methods of the invention.

In particular, the present invention provides kits for modulating a T-helper cell-mediated immune response in a subject, wherein the kits comprise a compound that binds to surface membrane immunoglobulin D (smIgD).

The present invention also provides kits for diagnosing a T helper cell-mediated immune disease in a subject, determining the susceptibility of a subject to a T helper cell-mediated immune disease and monitoring the responsiveness of a subject to therapy for a T helper cell-mediated immune disease, wherein the kits comprise means for obtaining a biological sample from the subject and means for quantifying the level of expression of surface membrane immunoglobulin D (smIgD), wherein level of expression of surface membrane immunoglobulin D (smIgD) is indicative of a T helper cell-mediated immune disease in a subject, the susceptibility of a subject to a T helper cell-mediated immune disease or the responsiveness of a subject to therapy for a T helper cell-mediated immune disease, respectively.

The present invention additionally provides kits for screening at least one candidate molecule for its capacity to modulate a T-helper cell-mediated immune response, wherein the kits comprise means for contacting the at least one candidate molecule with a biological sample and means for assaying for the level of binding of the at least one candidate molecule to surface membrane immunoglobulin D (smIgD) in the sample, wherein the level of binding of the at least one candidate molecule to smIgD is indicative of the capacity of the at least one candidate molecule to modulate a T-helper cell-mediated immune response.

The present invention moreover provides kits for screening at least one candidate molecule for its capacity to modulate a T-helper cell-mediated immune response, wherein the kits comprise means for contacting the at least one candidate molecule with a biological sample and means for assaying for the level of expression of at least one molecule selected from the group comprising GM-CSF, TNF-α and T-Bet, wherein the level of expression of the at least one molecule selected from the group comprising GM-CSF, TNF-α and T-Bet is indicative of the capacity of the at least one candidate molecule to modulate a T-helper cell-mediated immune response.

Typically, kits for carrying out a method of the invention contain all the necessary reagents to carry out the method. For example, in one embodiment the kit may comprise a first container containing a capture antibody raised against smIgD, and a second container containing a detection antibody raised against smIgD. The anti-smIgD capture antibody may be immobilized onto a solid surface, such as the well of a microtitre plate or a bead.

The anti-smIgD detection antibody may be conjugated to a marker such as biotin.

Typically, the kits described above will also comprise one or more other containers, containing for example, wash reagents, and/or other reagents capable of quantitatively detecting the presence of bound antibodies. For example, a signal generator such as a streptavidin peroxidase, may be provided for binding to the detection antibody, and a substrate such as 2,2'-azino-bis-(3-ethylbenzthiazoline-6-sulfonic acid) (ABTS) or tetramethylbenzidine (TMB) may be provided for binding to the signal generator.

Additionally or alternatively, kits of the invention may comprise a competitive ELISA, wherein IgD may be immobilized onto a solid surface. The immobilized IgD may then compete with endogenous smIgD present in test samples for binding with an anti-smIgD antibody. Additionally or alternatively, the anti-smIgD antibody may comprise a marker, for example, biotin, suitable for binding with a signal generator such as a streptavidin peroxidase.

In the context of the present invention, a compartmentalised kit includes any kit in which reagents are contained in separate containers, and may include small glass containers, plastic containers or strips of plastic or paper. Such containers may allow the efficient transfer of reagents from one compartment to another compartment whilst avoiding cross-contamination of the samples and reagents, and the addition of agents or solutions of each container from one compartment to another in a quantitative fashion. Such kits may also include a container which will accept the test sample, a container which contains the antibody(s) used in the assay, containers which contain wash reagents (such as phosphate buffered saline, Tris-buffers, and like), and containers which contain the detection reagent.

Typically, a kit of the present invention will also include instructions for using the kit components to conduct the appropriate methods.

Kits and methods of the invention may be used in conjunction with automated analysis equipment and systems, such as diagnostic systems enabling the analysis of multiple samples and/or multiple biomarkers, for example, the automated bead-based multiplexing BioRad BioPlex 2200 analyser. For example, an automated analyser may be used to determine the level of smIgD, GM-CSF, TNF-α and T-Bet, wherein the level is indicative of an autoimmune disease, an inflammatory disease or an allergic disease, or a predisposition thereto.

Methods and kits of the present invention are equally applicable to any animal, including humans, and also including but not limited to non-human primate, equine, bovine, ovine, caprine, leporine, avian, feline and canine species. Accordingly, for application to different species, a single kit of the invention may be applicable, or alternatively different kits, for example containing reagents specific for each individual species, may be required. Methods and kits of the present invention find application in any circumstance in which it is desirable to determine the level of smIgD, GM-CSF, TNF-α and T-Bet, wherein the level is indicative of an autoimmune disease, an inflammatory disease or an allergic disease, or a predisposition thereto.

Compositions and Methods of Treatment

Antibodies or other compounds for use in the methods described herein may be administered as compositions either therapeutically or preventively. In a therapeutic application, compositions are administered to a patient already suffering from a disease, in an amount sufficient to cure or at least partially arrest the disease and its complications. The composition should provide a quantity of the compound or agent sufficient to effectively treat the patient.

In general, suitable compositions may be prepared according to methods which are known to those of ordinary skill in the art and accordingly may include a pharmaceutically acceptable carrier, diluent and/or adjuvant.

Methods for preparing administrable compositions are apparent to those skilled in the art, and are described in more detail in, for example, *Remington's Pharmaceutical Science*, 15th ed., Mack Publishing Company, Easton, Pa., hereby incorporated by reference herein.

Compositions provided herein are commonly for parenteral administration, such as intravenous injection. Formulations and methods for the clinical or experimental administration of therapeutic or prophylactic antibodies by intravenous injection or infusion are well known in the art.

The compositions may be provided as topical formulations which comprise an active ingredient together with one or more acceptable carriers, diluents, excipients and/or adjuvants, and optionally any other therapeutic ingredients. Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by: autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which are incorporated herein by reference.

Dosages

The therapeutically effective dose level for any particular patient will depend upon a variety of factors including: the disorder being treated and the severity of the disorder; activity of the compound or agent employed; the composition employed; the age, body weight, general health, sex and diet of the patient; the time of administration; the route of administration; the rate of sequestration of the agent or compound; the duration of the treatment; drugs used in combination or coincidental with the treatment, together with other related factors well known in medicine.

One skilled in the art would be able, by routine experimentation, to determine an effective, non-toxic amount of agent or compound which would be required to treat applicable diseases.

Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 mg/m$^2$. Generally, an effective dosage is expected to be in the range of about 25 to about 50 mg/m$^2$, preferably about 25 to about 350 mg/m$^2$, more preferably about 25 to about 300 mg/m$^2$, still more preferably about 25 to about 250 mg/m$^2$, even more preferably about 50 to about 250 mg/m$^2$, and still even more preferably about 75 to about 150 mg/m$^2$.

Typically, in therapeutic applications, the treatment would be for the duration of the disease state.

Further, it will be apparent to one of ordinary skill in the art that the optimal quantity and spacing of individual dosages will be determined by the nature and extent of the disease state being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests.

Routes of Administration

The compositions of the present invention can be administered by standard routes. In general, the compositions may be administered by the parenteral (e.g., intravenous, intraspinal, subcutaneous or intramuscular), oral or topical route. Typically, administration is by the intravenous, intramuscular, subcutaneous or intraperitoneal route. The compositions can also be injected directly into the synovial joints or the site of inflammation.

Carriers, Diluents, Excipients and Adjuvants

Carriers, diluents, excipients and adjuvants must be "acceptable" in terms of being compatible with the other ingredients of the composition, and not deleterious to the recipient thereof. Such carriers, diluents, excipient and adjuvants may be used for enhancing the integrity and half-life of the compositions of the present invention. These may also be used to enhance or protect the biological activities of the compositions of the present invention.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrolidone; agar; gum tragacanth or gum acacia, and petroleum jelly. Typically, the carrier or carriers will form from 10% to 99.9% by weight of the compositions.

Other carriers may include viral-vectors in which DNA encoding the compounds of the present invention can be delivered directly into target cells.

The carriers may also include fusion proteins or chemical compounds that are covalently bonded to the compounds of the present invention. Such biological and chemical carriers may be used to enhance the delivery of the compounds to the targets or enhance therapeutic activities of the compounds. Methods for the production of fusion proteins are known in the art and described, for example, in Ausubel et al (In: Current Protocols in Molecular Biology. Wiley Interscience, ISBN 047 150338, 1987) and Sambrook et al (In: Molecular Cloning: A Laboratory Manual, Cold Spring Harbor Laboratories, New York, Third Edition 2001).

The compositions of the invention may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, in a form suitable for parenteral administration, that is, subcutaneous, intramuscular or intravenous injection.

For administration as an injectable solution or suspension, non-toxic parenterally acceptable diluents or carriers can include, Ringer's solution, isotonic saline, phosphate buffered saline, ethanol and 1,2 propylene glycol.

Some examples of suitable carriers, diluents, excipients and/or adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include Freund' adjuvants, emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Combination Therapies

Those skilled in the art will appreciate that the compositions may be administered as part of a combination therapy approach to the treatment of autoimmune diseases, inflammatory disease or allergy-related diseases, employing one or more of the compositions disclosed herein in conjunction with other therapeutic approaches to such treatment. For such combination therapies, each component of the combination may be administered at the same time, or sequentially in any order, or at different times, so as to provide the desired therapeutic effect. When administered separately, it may be preferred for the components to be administered by the same route of administration, although it is not necessary for this to be so. Alternatively, the components may be formulated together in a single dosage unit as a combination product. Suitable agents which may be used in combination with the compositions of the present invention will be known to those of ordinary skill in the art.

Timing of Therapies

Those skilled in the art will appreciate that the compositions may be administered as a single agent or as part of a combination therapy approach to the treatment of autoimmune diseases, inflammatory disease or allergy-related diseases at diagnosis or subsequently thereafter, for example, as follow-up treatment or consolidation therapy as a compliment to currently available therapies for such diseases. The compositions may also be used as preventative therapies for subjects who are genetically or environmentally predisposed to developing such diseases.

The present invention will now be described with reference to specific examples, which should not be construed as in any way limiting the scope of the invention.

EXAMPLES

Example 1

Methods and Materials 1.1 Isolation of PBMC

Human peripheral blood mononuclear cells (PBMC) were isolated by Ficoll-Paque Plus method (Amersham Bioscience) as described in the manufacturer's instruction. Briefly, whole blood from volunteers was collected into anticoagulating agents containing tubes. Freshly collected samples were immediately diluted with cold endotoxin-free phosphate buffer saline (PBS-E) at 1:1 ratio (volume:volume). The diluted blood sample was carefully layer over Ficoll-Paque Plus solution at 3:4 ratio (Ficoll volume:blood sample volume). Samples were then centrifuged at 400 g for 20-30 min at 16-20° C. to separate PBMC from plasma and red blood cells by density gradient. The layer containing PBMC was collected and washed 3 times with cold PBS-E. Viable cell counts were performed by trypan blue assay. It will be recognised that PBMC isolated using the technique described above comprises circulating T cells, B cells, monocytes and macrophages, and natural killer (NK) cells.

1.2. Cell Culture

Freshly isolated PBMC and cells from the Jurkat T-cell line were cultured in RPMI-1640 media supplemented with 10% fetal calf serum, 2 mM L-glutamine, 1 mM sodium pyruvate and antibiotics (100 U/ml penicillin and 100 U/ml streptomycin). Cells were kept in a humidified incubator at 37° C. and 5% $CO_2$. Cells were plated at $1.5-2 \times 10^6$ cells per well and cultured overnight prior to the start of experiments.

1.3 Gene Expression Analysis by Semi-Quantitative RT-PCR

PBMC and cells from the Jurkat T-cell line were plated at $1.5-2 \times 10^6$ cells per well overnight. Cells were treated with 50 µg/ml anti-human smIgD Ab (Serotec) or solvent control for 0, 3, 24 hrs prior to the treatment with 20 ng/ml PMA and 1 µg/ml Ionomycin (Sigma Aldrich) for 4 hrs. Cells were harvested at the end of PMA/Ionomycin treatment and washed once with PBS-E. Total mRNA was isolated by the Trizol method (Invitrogen) as described in the manufacturer's instruction. Samples of 0.5-1 µg mRNA were converted into cDNA using MMLV reverse transcriptase (Bioline). A sample of 3 µl of cDNA was subjected to PCR amplification using gene specific primers. The sequence of gene specific primers, the size of their PCR products and PCR conditions are listed in Table 1. PCR products were separated by 1% agarose gel electrophoresis and stained with ethidium bromide. DNA bands were visualized under UV and quantified by densitometry using a BioRad Gel Doc system and QuantityOne software (BioRad).

TABLE 1

Sequences and PCR conditions for semi-quantitative RT-PCR analysis

| Genes | Sequences | Tm (° C.) | PCR Product Sizes |
|---|---|---|---|
| T-Bet | Fwd 5'-GGGCGTCCAACAATGTGACCC-3' SEQ ID NO: 1<br>Rev 5'-CCTGGGGAACCACATCCTTCG-3' SEQ ID NO: 2 | 57.3 | 406 bp |
| GM-CSF | Fwd 5'-GAGCATGTGAATGCCATCCAGGAG-3' SEQ ID NO: 3<br>Rev 5'-TCCTGGACTGGCTCCCAGCAGTCAAA-3' SEQ ID NO: 4 | 57.3 | 390 bp |
| TNF-α | Fwd 5'-CGGGACGTGGAGCTGGCCGAGGAG-3' SEQ ID NO: 5<br>Rev 5'-CACCAGCTGGTTATCTCTCAGCTC-3' SEQ ID NO: 6 | 57.3 | 355 bp |
| IFN-γ | Fwd 5'-TGAAATATACAAGTTATATCTTGGCTTT-3' SEQ ID NO: 7<br>Rev 5'-GATGCTCTTCGACCTCGAAACAGCAT-3' SEQ ID NO: 8 | 57.3 | 501 bp |
| IL-2 | Fwd 5'-GAATGGAATTAATAATTACAAGAATCCC-3' SEQ ID NO: 9<br>Rev 5'-TGTTTCAGATCCCTTTAGTTCCAG-3' SEQ ID NO: 10 | 57.3 | 222 bp |
| β2M | Fwd 5'-ACCCCACTGAAAAAGATGA-3' SEQ ID NO: 11<br>Rev 5'-ATCTTCAAACCTCCATGATG-3' SEQ ID NO: 12 | 57.3 | 110 bp |

Example 2

Figure 2:
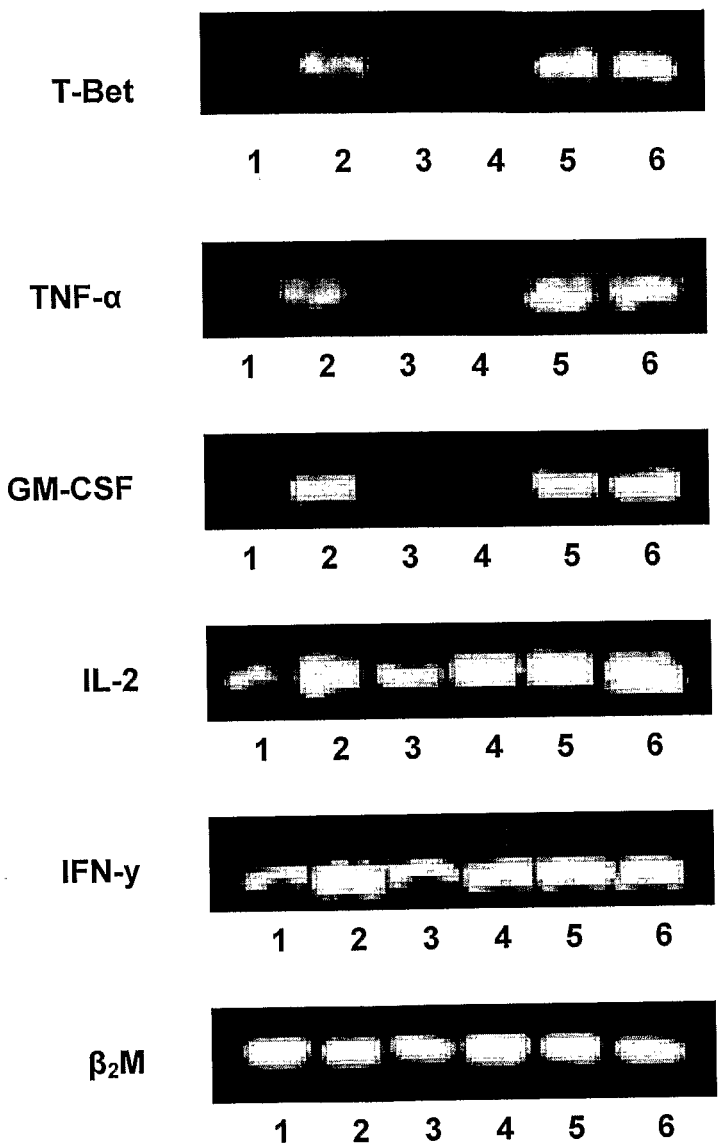
FIG. 2 provides images of the results of a representative RT-PCR analysis of Th 1-related gene expression in PBMC following treatment with anti-human smIgD Ab and PMA/Ionomycin. Cells were pre-treated with anti-human smIgD Ab at various time points prior to stimulation with PMA and Ionomycin for 4 hrs. Lane 1: solvent control; Lane 2: 20 ng/ml PMA and 1 µg/ml Ionomycin, 4 hrs; Lane 3: 50 µg/ml anti-human smIgD Ab alone, 24 hrs; Lane 4: 50 µg/m anti-human smIgD Ab,24 hrs and then PMA/Ionomycin, 4 hrs: Lane 5: 50 µg/m anti-human smIgD Ab, 3 hrs and then PMA/Ionomycin, 4 hrs; Lane 6: 50 µg/ml anti-human smIgD Ab and PMA/Ionomycin, 4 hrs. $β_2M$ gene was used as an internal quality and loading control. This figure is a representative of 2 or more independent experiments on PBMC from two different volunteers.

Priming Immune Cells with Anti-Human smIgD Ab Blocks PMA/Ionomycin-Induced Th1-Cytokine Gene Expression and its Transcriptional Regulator T-Bet The results presented in FIGS. 1 and 2 showed that treatment of the Jurkat T-cell line and PBMC with anti-human smIgD antibody (clone STAR94, Serotec, Oxford, UK) for 24 hrs, but not for 3 hrs, blocked PMA/Ionomycin-induced mRNA expression of GM-CSF, TNF-α and T-Bet. However, it was not effective in suppressing PMA/Ionomycin-induced gene expression of IFN-γ and IL-2 (FIGS. 1 and 2).

As expected, stimulation of Jurkat T-cells and PBMC induced a significant increase in mRNA expression of classical Th1-related cytokines and its transcriptional factor, including IFN-γ, IL-2, GM-CSF, TNF-α and T-Bet (FIGS. 1 and 2, lane 2), in comparison to the solvent control (FIGS. 1 and 2, lane 1). Treatment with anti-human smIgD Ab alone for 24 hrs did not have any significant effects on the basal mRNA expression of all of these genes (FIGS. 1 and 2, lane 3). Pre-treatment of the Jurkat T-cell line (FIG. 1, lane 5 and 6) and PBMC (FIG. 2, lane 4) with anti-human smIgD Ab for 24 hrs prior to stimulation with PMA/Ionomycin completely blocked the induction of mRNA expression of GM-CSF, TNF-α by PMA/Ionomycin and T-Bet but failed to inhibit PMA/Ionomycin-induced IFN-γ and IL-2 mRNA expression. Pre-treatment of PBMC with anti-human smIgD Ab for 3 hrs prior to or concurrent addition of anti-human smIgD Ab to PMA/Ionomycin stimulation failed to inhibit PMA/Ionomycin-induced mRNA expression of all the genes studied, including IFN-γ, IL-2, GM-CSF, TNF-α and T-Bet (FIGS. 1 and 2, lane 5 and 6).

These results indicate that the suppressive effect of anti-human smIgD Ab on PMA/Ionomycin-induced GM-CSF, TNF-α and T-Bet mRNA expression in PBMC is time-dependent. The addition of TGF-β1 appeared to enhance the suppressive effects of anti-human smIgD Ab on PMA/Ionomycin-induced GM-CSF expression but had no suppressive effect on PMA/Ionomycin-induced IFN-γ and IL-2 expression.

This data therefore indicated that treatment with anti-human smIgD Ab can specifically block PMA/Ionomycin-induced expression of the central regulator of Th1 immunity, T-bet, and suppress the amplification of the Th1 signal by T-bet. Treatment with anti-human smIgD Ab can also suppress the induction of two of the classical Th1 cytokines, TNF-α and GM-CSF, which have important roles in the pathogenesis of a number of autoimmune diseases.

The results also suggest that the negative or suppressive signal mediated via human smIgD acts downstream of PKC pathways and has differential effects on PKC-mediated immune responses.

Taken together, the data suggest that treatment with anti-human smIgD Ab can specifically suppress the induction of T-Bet, TNF-α, and GM-CSF during the activation of immune cells. The ineffectiveness of anti-human smIgD Ab in suppressing PMA/Ionomycin-induced IFN-γ and IL-2 expression in PBMC suggests that it dampens down Th1 immunity rather than completely suppresses the whole Th1 immune response.

Example 3

The Suppressive Effects of Anti-Human smIgD Ab on PMA/Ionomycin-Induced GM-CSF, TNF-α and T-Bet Expression are not Due to Cytotoxic Selection of Sub-Population of PBMC To examine whether treatment with anti-human smIgD Ab induced cell death in PBMC and hence selected out a sub-population of PBMC that have a defective PKC activation pathway, the inventors performed a viable cell count following each treatment.

A viable PBMC count was made using a trypan blue assay both in culture and following the treatments. PBMC were isolated and cultured as described in Example 1. Cells were plated out at $1.5 \times 10^6$ cell per well in a 12-well plate. There was no significant reduction in the number of viable PBMC after 24 h treatment with 50 µg/ml anti-human smIgD Ab and 4 hrs treatment with 20 ng/ml PMA and 1 µg/ml Ionomycin, when compared to the initial plating cell density with different treatments.

This result indicated that the in vitro treatment of PBMC with anti-human smIgD Ab at the dosage studied did not have any cytotoxic effects on human PBMC and the observed suppressive effects were not due to the selection of non-viable cells. Furthermore, the PKC activation pathway was functional and intact in these cells, as indicated by the normal induction of IFN-γ and IL-2 by PMA/Ionomycin in PBMC.

Example 4

The Expression of smIgD on Human Peripheral Blood Mononuclear Cells

To examine whether smIgD was expressed on different sub-populations of human immune cells, human PBMC were isolated were isolated from human blood from four volunteer subjects by the Ficoll-Paque Plus method as described in Example 1 and dually labeled for smIgD and cell markers. Briefly, PBMC were preincubated with species-specific serum to block any non-specific binding of antibody, and then incubated with fluorescent-conjugated antibodies. Given the important role of monocyte and T-cells in the production of Th1-cytokines and immune response, the expression of smIgD on these cells was examined by co-staining of monocyte (CD14) and T-cells (CD3) markers with smIgD. The goat FITC-conjugated anti-human IgD antibody (clone STAR94F) was purchased from Serotec, Oxford, UK. The PE-conjugated anti-human CD14 and CD3 antibodies were purchased from Dako Corporation (CA, USA). Antibodies were incubated with cells in the presence of blocking serum for 1 hour on ice. Cells were also incubated with appropriate antibody isotypes to control for non-specific isotype bindings. Cells were analyzed by flow cytometry using CellQuest program (Becton-Dickinson).

Figure 3:
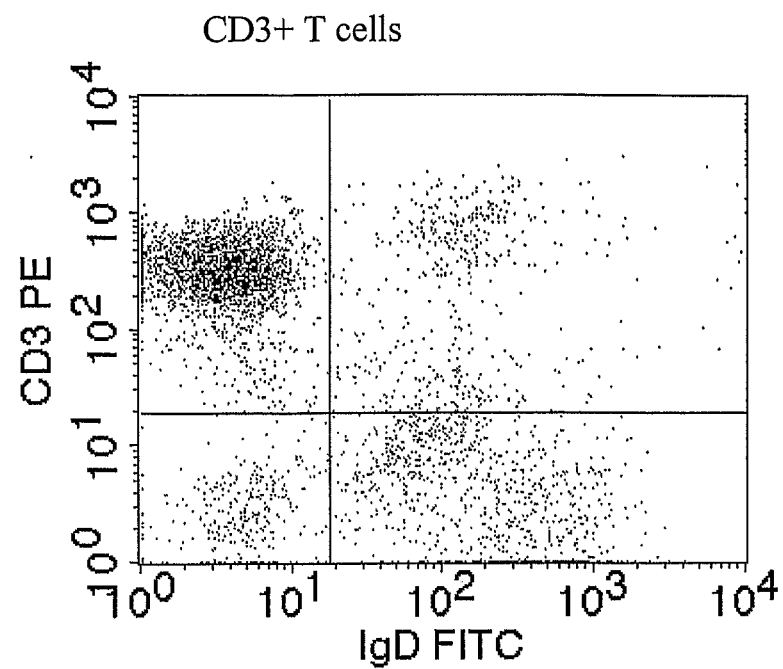
FIG. 3 provides results in dot plot form of a flow cytometry analysis of IgD labelling in CD3+ T cells (A) and CD14+ monocytes (B). 10,000 cells were counted per sample. The fluorescent intensity of IgD labelling is provided on the X-axis of each plot in arbitrary logarithmic units. The fluorescent intensity of CD3 labelling (A) or CD14 labelling (B) is provided on the Y-axis of each plot in arbitrary logarithmic units. The percentage of T-cells or monocytes expressing smIgD was calculated by gating out the cell population in the upper right quadrant of each panel.
Figure 3:
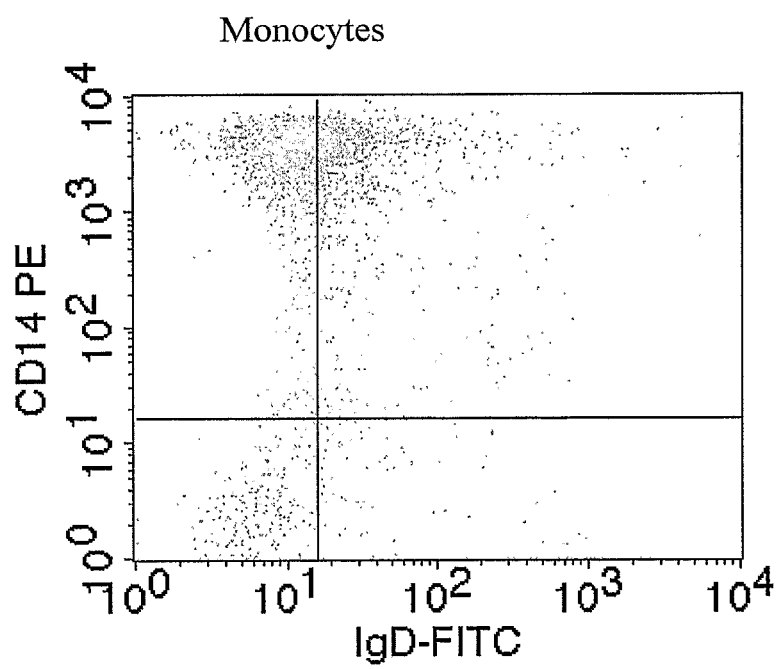

FIGS. 3A and 3B show results using dual-labeling for either the monocyte marker (CD14) or naïve T-cells (CD3) respectively, and smIgD. Approximately 10% of CD3+ T-cells expressed smIgD (FIG. 3A), represented by the cells present in upper right quadrant of the dot plot. Approximately 54% of CD14+ cells, representing cells of monocyte lineage, express smIgD (FIG. 3B). These dot plots are representative data from the volunteer subjects.

This data indicated that, unexpectedly, in human blood cells other than B cells, including a proportion of naïve T-cells and a proportion of cells of monocyte lineage appear to bear IgD on their cell surface membranes, and accordingly may be targeted using a compound which binds to smIgD, such as an antibody. Given the important roles of monocytes and T-cells and their Th1 cytokine production in the pathogenesis of inflammatory conditions, this data demonstrated that these cells are potential targets for treatment with anti-smIgD antibodies.

Example 5

The Suppressive Effect of Anti-Human smIgD Antibodies on PMA/Ionomycin-Induced T-Bet Protein Expression in Human PBMC The results presented in FIG. 2 illustrated that treatment with anti-human smIgD antibody caused a suppression of PMA/Ionomycin-induced T-Bet expression at message RNA (mRNA) level in PBMC. To examine whether treatment with anti-human smIgD antibody can suppress T-Bet protein production, human PBMC as prepared by the methods described in Example 1 were treated with 50 µg/ml of anti-human smIgD Ab (clone STAR94, Serotec, Oxford, UK) for 24 hours prior to or concurrently with PMA/Ionomycin (P/I) at 20 ng/ml and 1 µg/ml concentration for 6 hours, respectively.

Cells were harvested at the end of PMA/Ionomycin treatment and washed once with PBS-E. Total protein was isolated from the treated cells by the RIPA method and Western blotting was performed to assess the T-Bet protein level. Protein samples (30 µg) were separated on 10% acrylamide gel electrophoresis under denaturing conditions. Protein bands were then transferred onto nitrocellulose membrane which was then blocked with PBS/10% skim milk/0.1% BSA to prevent non-specific binding. Western blot membrane was probed with anti-human T-Bet antibody (clone 4B10, Santa Cruz Biotech. Inc, USA) in PBS/3% skim milk/0.1% BSA+0.3% Tween-20 at 4° C. overnight. Membranes were then washed and probed with secondary HRP-conjugated antibodies. Protein bands were visualised by X-ray film. The expression of house keeping gene actin was used as equal loading controls for western blotting.

Figure 4:
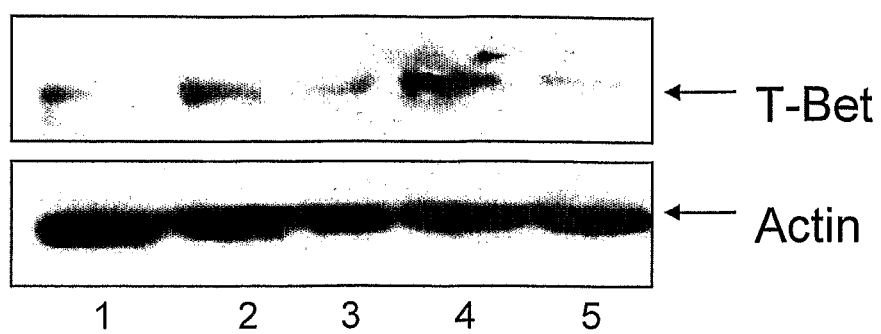
FIG. 4 provides an image of the result of Western blotting experiments described in Example 3. The Western blot for T-Bet expression shows the basal level of expression in untreated human PBMC (lane 1), elevated expression following 6 h stimulation with PMA/Ionomycin (lane 2), no change from the basal level of expression after incubation with anti-smIgD antibody alone (lane 3), elevated expression following concurrent incubation with anti-smIgD antibody and PMA/Ionomycin after 6 h (lane 4), and suppression of elevated expression following pre-treatment with anti-smIgD antibody followed by stimulation with PMA/Ionomycin (lane 5). The blot with actin expression was used as a quality and loading control.

FIG. 4 illustrates results showing the level of T-Bet protein expression as assessed by Western blotting. The basal expression of T-Bet protein in untreated human PBMC is shown in lane 1 of FIG. 4. As expected, T-Bet protein expression was induced in human PBMC following 6 h stimulation with PMA/Ionomycin in the absence of anti-human smIgD Ab treatment (lane 2). Lane 3 showed that there was no change in T-Bet protein expression from the basal level of T-Bet protein expression in human PBMC when treated with 50 µg/ml of anti-human smIgD antibody alone for 24 hours. Lane 4 shows that treatment of human PBMC with anti-human smIgD antibody concurrently with PMA/Ionomycin for 6 hours did not lead to a suppression of PMA/Ionomycin-induced T-Bet expression.

Taken together with data presented in FIG. 2, this data demonstrated that there is a concurrent suppression of PMA/Ionomycin-induced T-Bet expression at both mRNA and protein level in human PBMC exposed to anti-smIgD antibody.

Example 6

The Suppressive Effect of Anti-Human smIgD Antibodies on LPS-Induced TNF-α Expression in Human Monocyte Population The results presented in FIG. 2 demonstrated that treatment of human PBMC with anti-human smIgD antibodies caused a suppression of PMA/Ionomycin-Induced TNFα expression at the mRNA level. In order to investigate whether treatment with anti-human smIgD Ab can lead to a suppression of TNF-α at protein level, human PBMC were exposed to anti-human smIgD Ab for 24 h prior to stimulation with LPS (lipopolysacharide) and intra-cellular TNF-α protein expression was examined. LPS was used as a physiological stimulus of TNF-α production because it acts through the Toll-like receptor pathway, which is known to be involved in the pathogenesis of a number of autoimmune diseases. Cells of the monocyte lineage are sensitive to direct LPS stimulation, while T cells are not.

Briefly, PBMC were isolated as in Example 1 and then incubated with 50 µg/ml of anti-human smIgD Ab (clone STAR94, Serotec, Oxford, UK) at 24 hrs prior to or concurrently with the stimulation with LPS at 10 ng/ml final concentration. Cells were stimulated with 10 ng/ml LPS (Sigma Aldrich, Sydney, Australia) for the induction of TNF-α production.

Following the treatment, PBMC were stained for monocyte marker CD14 and intra-cellular TNF-α using specific antibodies conjugated with a fluorescent label. Briefly, 1×10⁶ cells were resuspended in 50 µl of PBS/0.1% BSA and incubated with 50 µg/ml of FITC-conjugated anti-human CD14 Ab (Dako Corporation, USA) for 45 min on ice. Cells were then fixed overnight with 1% Befeldin A. Cells were then permeablized by incubating in PBS/0.1% saporin/0.1% BSA for 20 min on ice. Cells were then stained for intra-cellular TNF-α protein expression by incubating with 50 µg/ml of PE-conjugated anti-human TNF-α Ab in 50 µl PBS/0.1% saporin/0.1% BSA for 45 min on ice. Cells were washed twice with PBS before analysis by flow cytometry. Monocytes expressing TNF-α were detected by flow cytometry using CellQuest program (Becton Dickinson).

Figure 5:
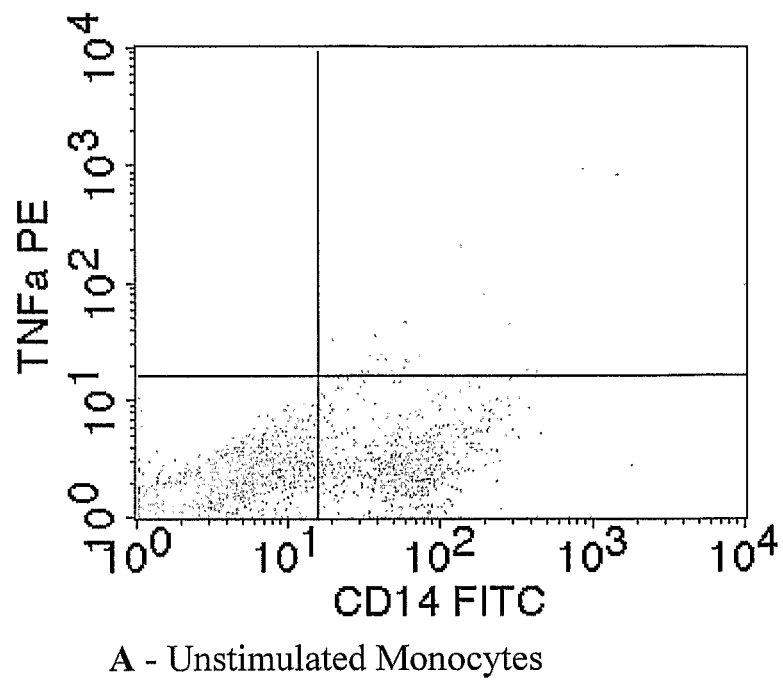
FIG. 5 provides representative results in dot plot form of a flow cytometry analysis of TNF-α production in human monocytes following treatment with anti-human smIgD and LPS stimulation (n=3). The X-axis of each dot plot corresponds to the fluorescent intensity of CD14 labelling, and the Y axis of each plot corresponds to the fluorescent intensity of TNF-α labelling. Both axes are presented in the same arbitrary logarithmic units. A is a representative dot plot analysis of an untreated monocyte sample (with the upper right quadrant the TNF-α positive CD14 labelled cells). B is a representative analysis of a monocyte sample stimulated with 10 ng/ml LPS for 4 h. C is a representative analysis of a monocyte sample following treatment with anti-human smIgD Ab for 24 h. D is a representative analysis of a monocyte sample following treatment with anti-human smIgD Ab concurrently with LPS for 4 hrs. E is a representative analysis of a monocyte sample following treatment with anti-human smIgD Ab for 24 h prior to LPS stimulation.
Figure 5:
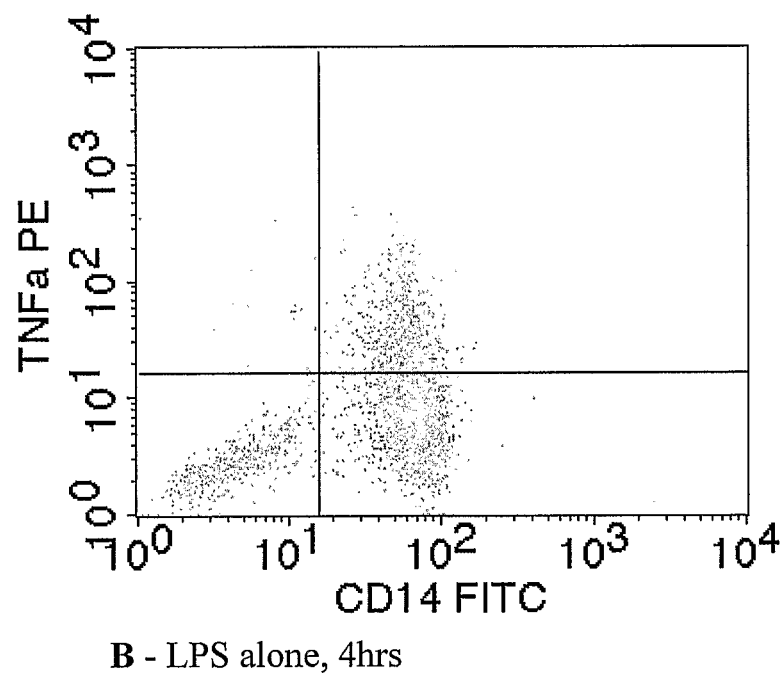
Figure 5:
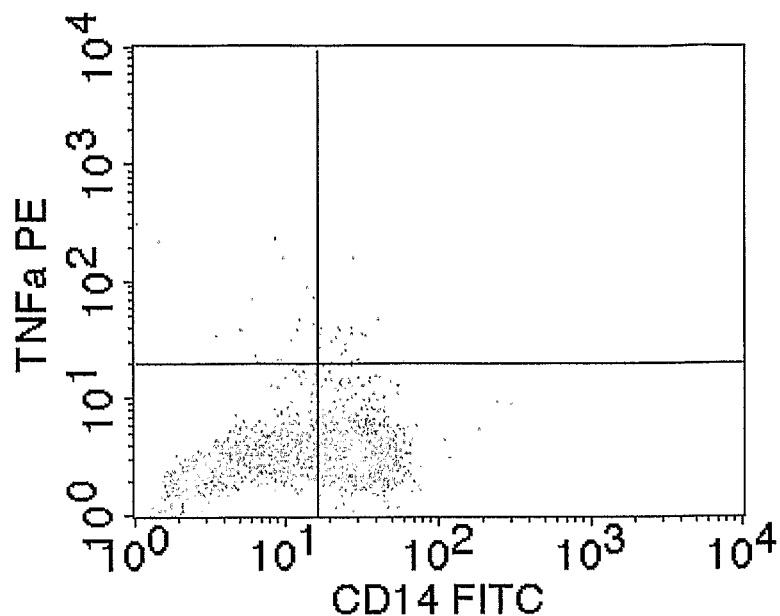
Figure 5:
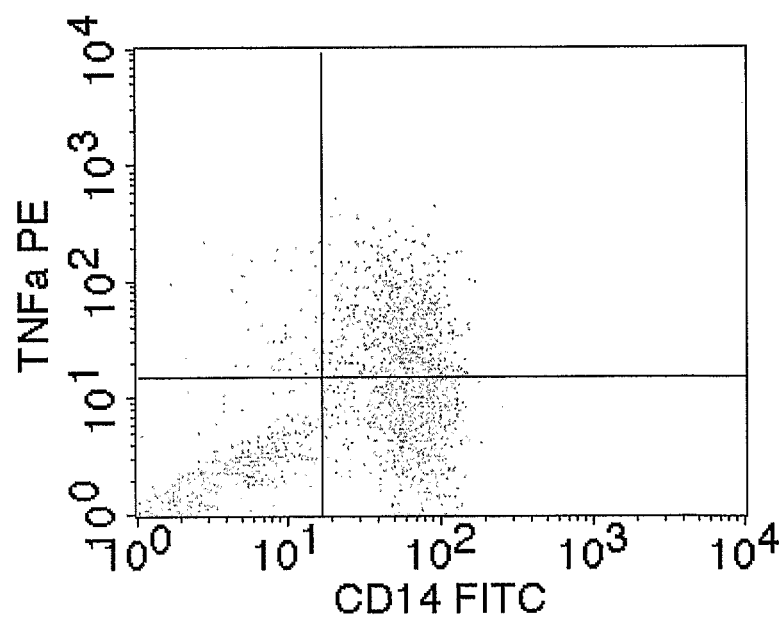
Figure 5:
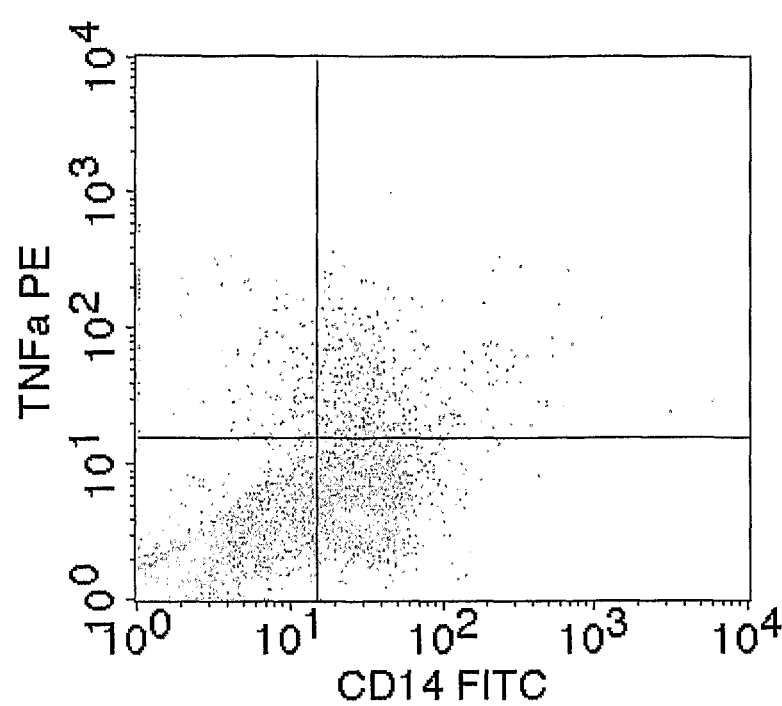

The results of this experiment are illustrated in FIG. 5. Each plot in FIG. 5 shows a representative flow cytometric analysis of TNF-α production in human monocyte following treatment with anti-human smIgD and LPS stimulation (n=3). Panel A is a representative a dot plot analysis of an untreated monocyte sample (upper right quadrant of Panel A, FIG. 5). This result shows that unstimulated human monocytes have little or no expression of intra-cellular TNF-α. When stimulated with 10 ng/ml LPS for 4 hrs, approximately 25% of human monocyte population expressed intra-cellular TNF-α (upper right quadrant in Panel B, FIG. 5), indicating LPS induced TNF-α production in human monocyte population. Treatment with anti-human smIgD Ab alone for 24 hrs did not induce TNF-α production in human monocytes (upper right quadrant in Panel C, FIG. 5). Treatment with anti-human smIgD Ab concurrently with LPS for 4 hours induced intra-cellular TNF-α production in approximately 26% of the human monocyte population, indicating that concurrent treatment with anti-human smIgD Ab and LPS did not suppress LPS-induced TNF-α production in human monocyte (upper right quadrant in Panel D, FIG. 5). Treatment with anti-human smIgD Ab 24 hrs prior to LPS stimulation, however, resulted in a dramatically reduced proportion (5%) of cells of the monocyte population in which intracellular TNF-α was expressed (upper right quadrant in Panel E, FIG. 5).

These data demonstrate that pretreatment by anti-smIgD Ab can suppress LPS-induced TNF-α production in human monocytes. Given the important roles of monocytes and their TNF-α production in Th1-related inflammatory conditions, these data demonstrate the therapeutic potential of anti-human smIgD Ab in suppressing TNF-ααproduction in such conditions.

Example 7

Treatment with Anti-IgD Antibody Reduced Incidence of Severe Joint Inflammation in a Collagen-Induced Arthritis (CIA) Mouse Model Experiments to examine the therapeutic effects of systematic administration of anti-mIgD Ab in preventing and reducing joint inflammation in collagen-induced arthritis (CIA) in DAB/1J strain mice were performed. CIA in DAB/1J strain mice is a well-established and generally recognized in vivo model of Th1-related inflammation, with the physiology and aetiology of the disease in the model reflecting many characteristics of human inflammatory conditions, including the involvement of CD4+ T-cells and the overproduction of Th1 cytokines.

To examine the therapeutic and side-effects of the administration of anti-mIgD Ab, mice were divided into 3 treatment groups: (1) CIA induction, (2) anti-mIgD Ab treatment before CIA induction, and (3) CIA induction before anti-mIgD Ab treatment. Each group contained 10 male DAB/1J mice of between 6-7 weeks old (Gore Hill Animal Laboratory, UTS). The welfare of all experimental animals was monitored and all experimental procedures were performed in accordance with the Royal North Shore Hospital and University of Technology Sydney ACEC's guidelines.

For CIA induction, mice were injected at the base of the tail subcutaneously with 200 µl of 4 mg/ml bovine type-II collagen (BII) in Freund's adjuvant (CFA) solution (Sigma Aldrich) supplemented with 4 mg/ml *M Tuberculosis* antigen (Sigma Aldrich), A second injection with BII/CFA solution was given 21 days later to boost the onset of CIA. In untreated animals, the onset of joint inflammation is usually observable 3 to 4 days after the second injection.

The clinical severity of CIA was evaluated using an established scoring system as follows: 0 points=no swelling, 1 point=swelling and redness in one digit or mild edema, 2 points=moderate swelling and redness in 2 digits, 3 points=moderate swelling and redness in 3 digits, and 4 points=swelling and redness in all 4 digits, whole paw and ankle or the inability to cling to a wire grid.

To examine the preventive effects of anti-mIgD Ab on inflammation in CIA, mice were given a daily intravenous injection of 10 mg per kg of body weight of goat anti-mouse mIgD Ab (Clone AMS-9.1, BD Pharmigen, USA) for 3 days prior to the second BIII/CFA injection. For the therapeutic study group, mice were given the same anti-mIgD Ab treatment as the preventive study group but 3 days after the first observable sign of inflammation.

The clinical severity of CIA was evaluated daily for 11 days after the second BII/CFA injection. All mice survived the administration of the anti-mIgD with no observed side effects. The clinical score and incidence of arthritis was evaluated by the investigators and independent observers who were blinded to the treatments.

Figure 6:
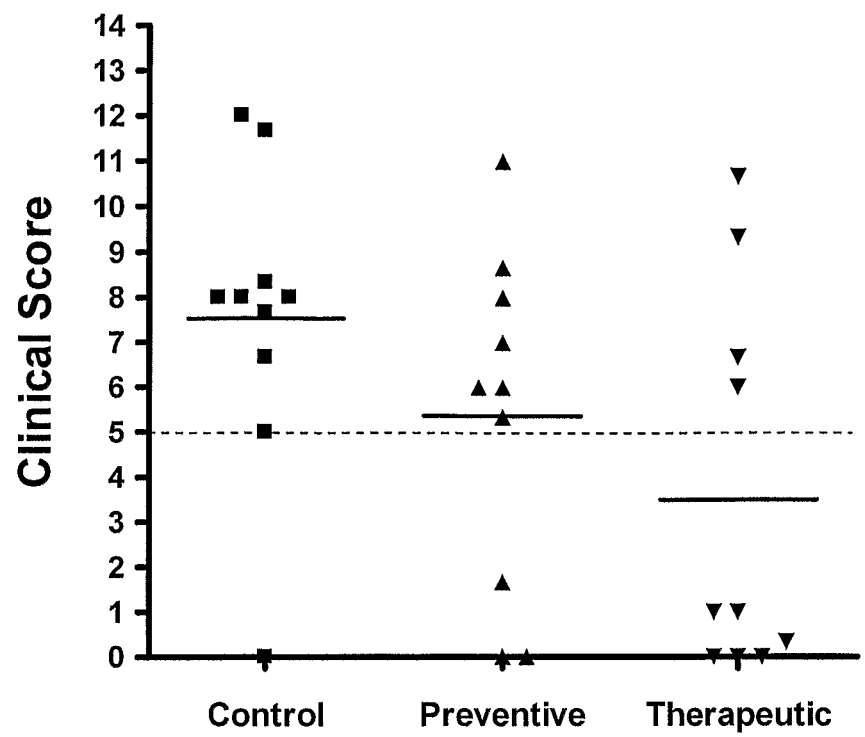
FIG. 6 provides a graphical illustration of the results of collagen-induced arthritis experiments described in Example 7. Individual points represent the results of clinical scoring of a single animal at day 11. The mean clinical score for each group is provided as a short horizontal bar. The dotted line at the level of clinical score 5 represents the transition between severe disease (above the line) and non-severe disease (below the line).
Figure 7:
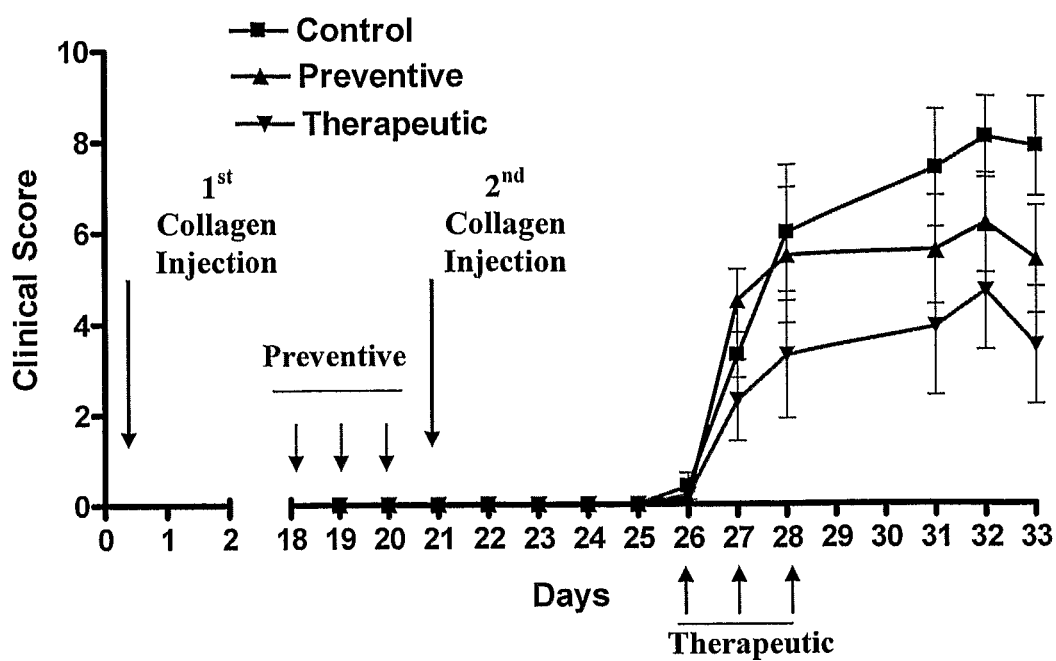
FIG. 7 provides a graphical illustration of the progression of clinical scores in the collagen-induced arthritis model for the control, preventative and therapeutic groups of animals. Arrows indicate time of injection for the preventative and therapeutic administration of anti-smIgD. Values are expressed as the mean clinical score±SEM (n=10 for each group).

FIG. 6 show the clinical score of individual mouse in each group of treatment (n=10). Statistical analysis showed that the mean and standard error of mean clinical score for the control, preventive and therapeutic groups was 7.5±1.1, 5.3±1.3 and 3.5±1.3 respectively. When severe disease is defined as a score of >5 (represented by dotted line in FIG. 5), only 1/10 (10%) animal in the control group had a clinical score of 5 or less, compared to 4/10 (40%) and 6/10 (60%) in the preventive and therapeutic groups, respectively.

This data indicates that the preventive and therapeutic treatment with anti-smIgD Ab resulted in a reduction in the incidence of severe inflammation by 25% and 50% respectively. A Chi-Square test between the control group and the combined group of preventive and therapeutic treatment showed a P value <0.05, indicating there was a statistically significant difference in the incidence of severe inflammation between the control group and the group of mice that received anti-smIgD antibody. This result demonstrated the therapeutic potential of anti-smIgD Ab in reducing the incidence of severe inflammation in vivo.

Example 8

Composition for Administration

A composition for parenteral injection may be prepared to contain 0.05 mg to 5 g of a suitable agent or compound as disclosed herein in 10 mls to 2 litres of 1% carboxymethylcellulose. Similarly, a composition for intravenous infusion may comprise 250 ml of sterile Ringer's solution, and 0.05 mg to 5 g of a suitable agent or compound as disclosed herein.

A composition of a suitable agent or compound in the form of a capsule may be prepared by filling a standard two-piece hard gelatin capsule with 500 mg of the agent or compound, in powdered form, 100 mg of lactose, 35 mg of talc and 10 mg of magnesium stearate.

In accordance with the best mode of performing the invention provided herein, specific preferred compositions are outlined below. The following are to be construed as merely illustrative examples of compositions and not as a limitation of the scope of the present invention in any way.

The invention claimed is:

1. A method for suppressing an autoimmune disease in a human subject in need thereof, the method comprising administering to the subject a therapeutically effective amount of a compound comprising an unconjugated humanized monoclonal antibody that binds specifically to the delta chain of surface membrane immunoglobulin D (smIgD) sufficient to suppress an autoimmune disease in a human subject, wherein binding of the unconjugated humanized monoclonal antibody to smIgD results in cross-linking of smIgD.

2. The method according to claim 1, wherein binding of the unconjugated humanized monoclonal antibody to smIgD results in suppression of expression of at least one molecule selected from the group comprising GM-CSF, TNF-α and T-Bet.

3. The method according to claim 2, wherein the suppression of expression of the at least one molecule results in suppression of a Th1 immune response.

4. The method according to claim 2, wherein the suppression of expression of the at least one molecule results in activation of a Th2 immune response.

5. The method according to claim 1, wherein said method further comprises administration of a further molecule, wherein the further molecule contributes to modulating a T-helper cell or monocyte lineage cell-mediated immune response.

* * * * *